(12) United States Patent
Hayakawa et al.

(10) Patent No.: US 11,897,742 B2
(45) Date of Patent: Feb. 13, 2024

(54) CAP STERILIZATION DEVICE AND CONTENT FILLING SYSTEM

(71) Applicant: Dai Nippon Printing Co., Ltd., Tokyo (JP)

(72) Inventors: Atsushi Hayakawa, Tokyo (JP); Seiji Kuwano, Tokyo (JP); Yoshinori Satou, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 17/756,568

(22) PCT Filed: Oct. 20, 2020

(86) PCT No.: PCT/JP2020/039465
§ 371 (c)(1),
(2) Date: May 27, 2022

(87) PCT Pub. No.: WO2021/111750
PCT Pub. Date: Jun. 10, 2021

(65) Prior Publication Data
US 2023/0002208 A1  Jan. 5, 2023

(30) Foreign Application Priority Data

Dec. 4, 2019 (JP) .................................. 2019-219685

(51) Int. Cl.
*B67B 3/00* (2006.01)
*B67C 7/00* (2006.01)

(52) U.S. Cl.
CPC ............ *B67B 3/003* (2013.01); *B67C 7/0073* (2013.01)

(58) Field of Classification Search
CPC .......... B65B 55/10; B65B 55/04; B67B 3/00; B67B 3/003; B67C 7/00; B67C 7/0073
(Continued)

(56) References Cited

U.S. PATENT DOCUMENTS

| 8,945,477 B2 | 2/2015 | Ceci et al. |
| 2019/0337786 A1 | 11/2019 | Hayakawa et al. |

FOREIGN PATENT DOCUMENTS

| CN | 109153470 A | 1/2019 |
| EP | 4 071 063 A1 | 10/2022 |

(Continued)

OTHER PUBLICATIONS

Japanese Office Action (Application No. 2021-123445) dated Jul. 29, 2022 (with English translation).
(Continued)

*Primary Examiner* — Jacob A Smith
(74) *Attorney, Agent, or Firm* — BURR PATENT LAW, PLLC (57) ABSTRACT

A cap sterilization device (50) includes a sterilant spraying chamber (52) in which a sterilant is sprayed onto a cap (33) and an air-rinsing chamber (53) in which the cap (33) onto which the sterilant has been sprayed in the sterilant spraying chamber (52) is subjected to air-rinsing. A sterilant spraying wheel (74) that conveys the cap (33) while rotating the cap (33) is disposed in the sterilant spraying chamber (52). An air-rinsing wheel (75) that conveys the cap (33) onto which the sterilant has been sprayed while rotating the cap (33) is disposed in the air-rinsing chamber (53). The air-rinsing chamber (53) is disposed vertically above the sterilant spraying chamber (52).

7 Claims, 7 Drawing Sheets

(58) Field of Classification Search
USPC .......................................................... 53/167
See application file for complete search history.

(56) References Cited

FOREIGN PATENT DOCUMENTS

| | | | | | |
|---|---|---|---|---|---|
| JP | S61-047323 | A | | 3/1986 | |
| JP | H03-34308 | Y2 | * | 7/1991 | ............... B08B 3/02 |
| JP | H03-034308 | Y2 | | 7/1991 | |
| JP | H06-293319 | A | | 10/1994 | |
| JP | 11189218 | A | * | 7/1999 | ............. B65B 55/10 |
| JP | H11-189218 | A | | 7/1999 | |
| JP | 3791868 | B2 | | 6/2006 | |
| JP | 2011-011811 | A | | 1/2011 | |
| JP | 2013091518 | A | * | 10/2011 | ............... B67C 7/00 |
| JP | 2012-500759 | A | | 1/2012 | |
| JP | 2016-064346 | A | | 4/2016 | |
| JP | 2016064346 | A | * | 4/2016 | ............... B08B 3/02 |
| JP | 2017-214107 | A | | 12/2017 | |
| JP | 2018-122927 | A | | 8/2018 | |
| JP | 2021-088388 | A | | 6/2021 | |
| WO | 2017/209185 | A1 | | 12/2017 | |

OTHER PUBLICATIONS

Japanese Office Action (Application No. 2021-123445) dated Dec. 2, 2022 (with English translation).
International Search Report and Written Opinion (Application No. PCT/JP2020/039465) dated Jan. 12, 2021 (with English translation).
Japanese Office Action (Application No. 2019-219685) dated Dec. 4, 2020 (with English translation).
Japanese Office Action (Application No. 2019-219685) dated Mar. 26, 2021 (with English translation).
English translation of International Preliminary Report on Patentability (Chapter 1) Application No. PCT/JP2020/039465 dated Jun. 16, 2022, 5 pages.
Chinese Office Action (with English translation) dated Apr. 12, 2023 (Application No. 202080083610.6).
Extended European Search Report dated Dec. 12, 2023 (Application No. 20895391.9).

* cited by examiner

CAP STERILIZATION DEVICE AND CONTENT FILLING SYSTEM

TECHNICAL FIELD

The present disclosure relates to a cap sterilization device and a content filling system.

BACKGROUND ART

A sterile filling system (aseptic filling system) that fills a sterilized container (PET bottle) with a sterilized content in a sterile environment and then closes the container with a cap is known. More specifically, in the sterile filling system, first, a molded container is supplied to the sterile filling system. Next, an aqueous hydrogen peroxide solution, which serves as a sterilant, is sprayed onto the container in the sterile filling system. After that, the sterilant is dried so that the container is sterilized. Next, the container is aseptically filled with a content. There is also another method for filling a sterilized container with a sterilized content in a sterile environment. In the other method, a small amount of sterilant is applied dropwise to an inner surface of the container when the container is molded. Next, the mouth of the container is sealed, and the inner surface of the container is sterilized with vapor of the sterilant (hydrogen peroxide) that is vaporized. Then, the sterilized container is supplied to the sterile filling system. After that, the outer surface of the container is sterilized in the sterile filling system, and then the mouth is opened and the container is aseptically filled with a content.

To produce a product by filling a container with a content and closing the container with a cap in the sterile filling system, it is necessary to sterilize the cap as well as the container. Patent Documents 1 to 5 describe examples of a cap sterilization device for sterilizing a cap.

However, it may be difficult to reduce the size of the cap sterilization device according to the related art. When the size of the cap sterilization device is large, there is a possibility that the capital investment costs and the costs of chemical agents used for sterilization, thermal energy, or cleaning water will be increased. Therefore, it is desirable to reduce the size of the cap sterilization device.

PRIOR ART REFERENCES

Patent Documents

Patent Document 1: Japanese Unexamined Patent Application Publication No. 6-293319
Patent Document 2: Japanese Unexamined Patent Application Publication No. 2011-11811
Patent Document 3: Japanese Unexamined Patent Application Publication No. 2012-500759
Patent Document 4: Japanese Unexamined Patent Application Publication No. 2017-214107
Patent Document 5: Japanese Unexamined Patent Application Publication No. 2018-122927

The present disclosure has been made in consideration of the above-described circumstances, and an object of the present disclosure is to provide a cap sterilization device and a content filling system that can be reduced in size.

SUMMARY OF INVENTION

A cap sterilization device according to an embodiment includes a sterilant spraying chamber in which a sterilant is sprayed onto a cap; and an air-rinsing chamber in which the cap onto which the sterilant has been sprayed in the sterilant spraying chamber is subjected to air-rinsing. A sterilant spraying wheel that conveys the cap while rotating the cap is disposed in the sterilant spraying chamber. An air-rinsing wheel that conveys the cap onto which the sterilant has been sprayed while rotating the cap is disposed in the air-rinsing chamber. The air-rinsing chamber is disposed vertically above the sterilant spraying chamber.

In the cap sterilization device according to the embodiment, a plurality of the air-rinsing wheels may be provided, and one of the air-rinsing wheels may have a rotation center axis positioned above a rotation center axis of another one of the air-rinsing wheels that is positioned upstream of the one of the air-rinsing wheels in a conveying direction of the cap.

In the cap sterilization device according to the embodiment, the air-rinsing chamber may include a protruding portion that protrudes sideways beyond the sterilant spraying chamber, and a sterilant spraying device that supplies the sterilant to the cap may be disposed on a side of the sterilant spraying chamber, the sterilant spraying device being disposed in a housing space positioned below the protruding portion.

The cap sterilization device according to the embodiment may further include a cleaning chamber in which the cap that has been subjected to air-rinsing in the air-rinsing chamber is cleaned, the cleaning chamber being disposed above the protruding portion.

In the cap sterilization device according to the embodiment, liquid present in the air-rinsing chamber may be discharged through the sterilant spraying chamber.

The cap sterilization device according to the embodiment may further include a conveying chute along which the cap that has been subjected to air-rinsing is conveyed downstream. An inclination angle of the conveying chute with respect to a horizontal plane may be 10° or more and 90° or less.

A content filling system according to an embodiment includes a bottle sterilization device that sterilizes a bottle; a filling device that fills the bottle with a content; the cap sterilization device according to the present disclosure that sterilizes the cap; and a cap attaching device that attaches the sterilized cap to a mouth of the bottle filled with the content by the filling device.

According to the present disclosure, the cap sterilization device and the content filling system can be reduced in size.

DESCRIPTION OF EMBODIMENTS

Figure 1:
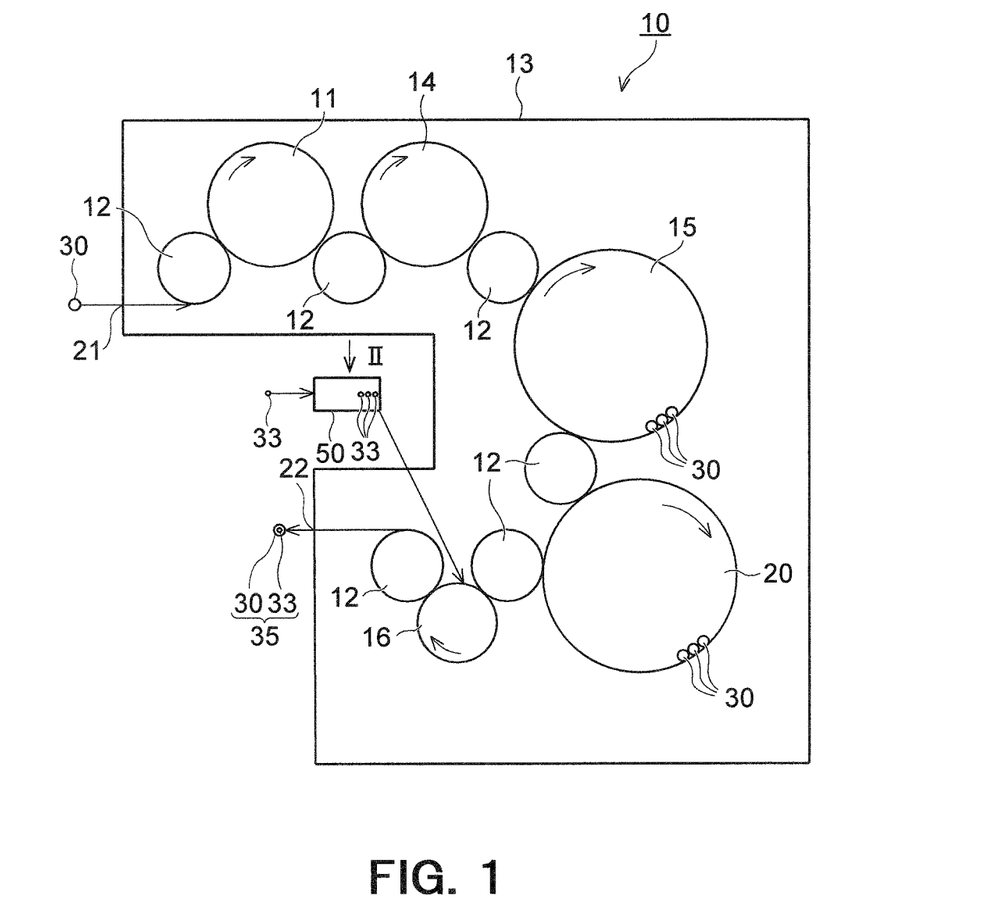
FIG. 1 is a schematic plan view of a content filling system according to an embodiment of the present disclosure.
Figure 2:
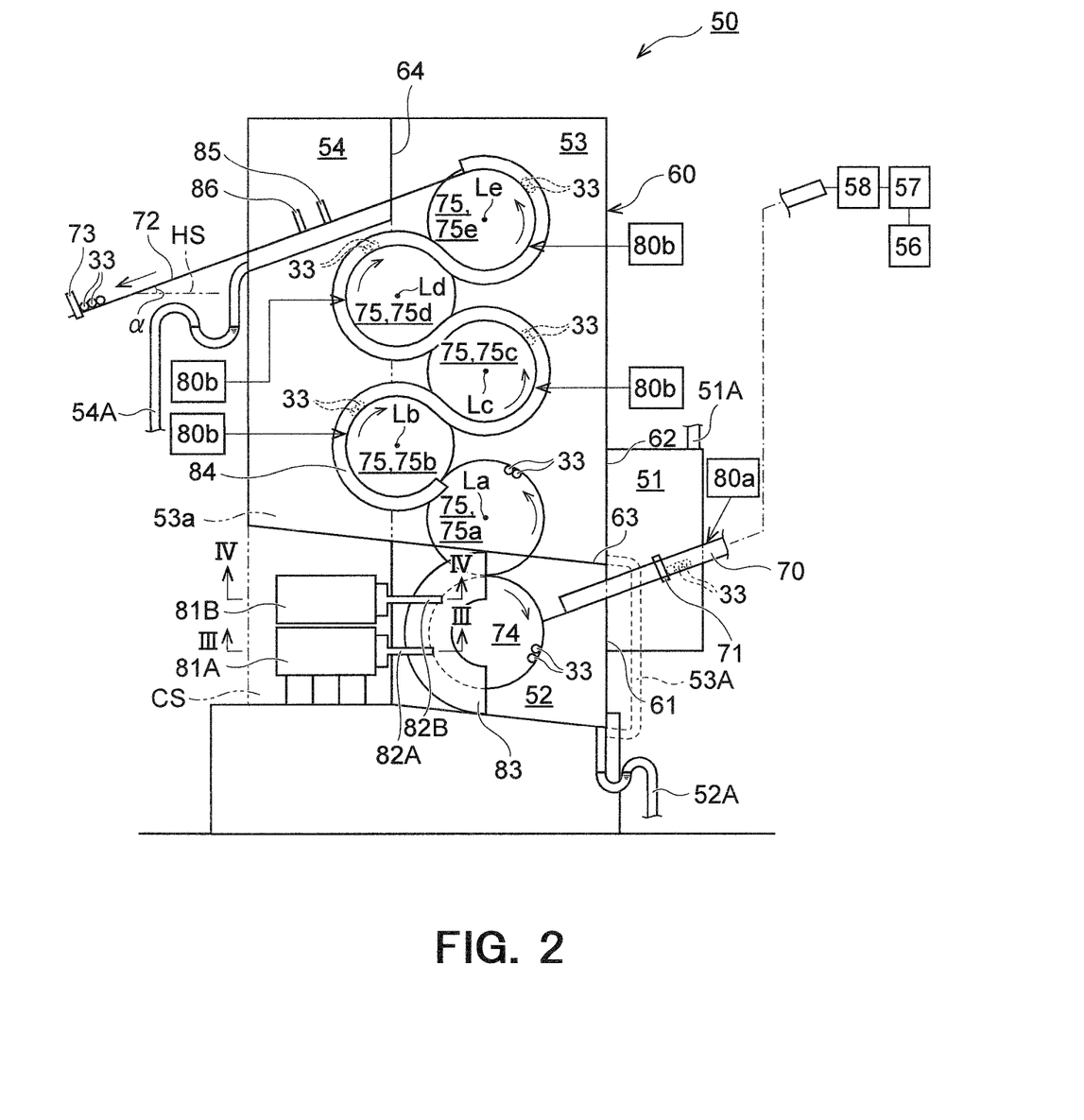
FIG. 2 is a schematic front view of a cap sterilization device according to the embodiment of the present disclosure (viewed along arrow II in FIG. 1).

An embodiment will now be described with reference to the drawings. FIGS. 1 and 2 illustrate the embodiment. Drawings referred to below are schematic diagrams. Therefore, sizes and shapes of components are exaggerated as appropriate to facilitate understanding. Changes are possible as appropriate without departing from the technical idea. In each of the drawings described below, the same parts are denoted by the same reference signs, and detailed description thereof may be omitted. The numerical values of dimensions, for example, and materials of components described in this specification are examples of the embodiment. The numerical values and materials are not limited to the examples, and may be selected as appropriate. In this specification, terms relating to shapes and geometric conditions, such as "parallel", "orthogonal", and "perpendicular", are to be interpreted not only in a strict sense but also to cover states that are substantially the same as those in a strict sense.

(Content Filling System)

A content filling system (sterile filling system, aseptic filling system) according to the present embodiment will be described with reference to FIG. 1.

A content filling system 10 illustrated in FIG. 1 is a system for filling bottles 30 with a content, such as a beverage. The bottles 30 may be produced by performing biaxial stretching blow molding on preforms formed by injection molding of a synthetic resin material. The material of the bottles 30 is preferably a thermoplastic resin, in particular, polyethylene (PE), polypropylene (PP), polyethylene terephthalate (PET), or polyethylene naphthalate (PEN). The containers may each be composed of glass, a can, paper, a pouch, or a composite container thereof. In the present embodiment, it is assumed that the containers are bottles made of a synthetic resin.

As illustrated in FIG. 1, the content filling system 10 includes a bottle supplying unit 21, a bottle sterilization device 11, an air-rinsing device 14, a sterile-water-rinsing device 15, a filling device (filler) 20, and a cap attaching device (capper, a closing-and-capping machine) 16, and a product bottle carry-out unit 22. The bottle supplying unit 21, the bottle sterilization device 11, the air-rinsing device 14, the sterile-water-rinsing device 15, the filling device 20, the cap attaching device 16, and the product bottle carry-out unit 22 are arranged in that order from the upstream side toward the downstream side in a conveying direction of the bottles 30. A plurality of conveying wheels 12 are provided between the bottle sterilization device 11, the air-rinsing device 14, the sterile-water-rinsing device 15, the filling device 20, and the cap attaching device 16 to convey the bottles 30 between these devices.

The bottle supplying unit 21 successively receives empty bottles 30 to be supplied to the content filling system 10 from the outside, and conveys the received bottles 30 to the bottle sterilization device 11.

A bottle molding unit (not illustrated) that molds the bottles 30 by performing biaxial stretching blow molding on preforms may be disposed upstream of the bottle supplying unit 21. Thus, processes of supplying the preforms, molding the bottles 30, filling the bottles 30 with a content, and closing the bottles 30 may be successively performed. In such a case, the preforms, which are small in volume, may be transported from the outside to the content filling system 10 instead of the bottles 30 having a large volume. Therefore, the size of the facility including the content filling system 10 can be reduced.

The bottle sterilization device 11 sterilizes the interiors of the bottles 30 by spraying a sterilant into the bottles 30. The sterilant may be, for example, an aqueous hydrogen peroxide solution. In the bottle sterilization device 11, the aqueous hydrogen peroxide solution having a concentration of 1% by weight of more, preferably 35% by weight, is temporarily vaporized, and then condensed to generate mist or gas. The mist or gas is sprayed onto the inner and outer surfaces of the bottles 30. Since the interiors of the bottles 30 are sterilized with the aqueous hydrogen peroxide solution in the form of mist or gas, the inner surfaces of the bottles 30 are uniformly sterilized.

The air-rinsing device 14 supplies sterile heated air or room temperature air to each bottle 30 to remove foreign matter, hydrogen peroxide, etc. from the bottles 30 while activating the hydrogen peroxide.

The sterile-water-rinsing device 15 receives the bottles 30 sterilized with hydrogen peroxide, which is the sterilant, and cleans the bottles 30 with sterile water at a temperature of 15° C. or more and 85° C. or less. Thus, the hydrogen peroxide that has adhered to the bottles 30 is rinsed off, and foreign matter is removed.

The filling device 20 fills the bottles 30 with a content sterilized in advance through the mouths of the bottles 30. The filling device 20 introduces the content into the bottles 30 in an empty state. The filling device 20 introduces the content into the bottles 30 while rotating (revolving) the bottles 30. The content may be introduced into the bottles 30 at a room temperature. The content is sterilized by being heated, for example, in advance and then cooled to a room temperature of 3° C. or more and 40° C. or less before being introduced into the bottles 30. The content with which the bottles 30 are filled by the filling device 20 may be, for example, a beverage, such as a tea-based beverage or a milk-based beverage.

The cap attaching device 16 closes the bottles 30 that have been filled with the content by the filling device 20 by attaching caps 33 to the mouths of the bottles 30. The cap attaching device 16 closes the mouths of the bottles 30 with the caps 33 to seal the bottles 30 and prevent entrance of external air and microbes into the bottles 30. The cap attaching device 16 attaches the caps 33 to the mouths of the bottles 30 filled with the content while rotating (revolving) the bottles 30. Thus, product bottles 35 are obtained by attaching the caps 33 to the mouths of the bottles 30.

The caps 33 are sterilized in advance by a cap sterilization device 50. The cap sterilization device 50 is, for example, disposed outside a sterile chamber 13 (described below) and near the cap attaching device 16. The caps 33 are conveyed into the cap sterilization device 50 from the outside, and are successively conveyed to the cap attaching device 16. While the caps 33 are being conveyed toward the cap attaching device 16, hydrogen peroxide in the form of mist or gas is blown against the inner and outer surfaces of the caps 33. After that, the caps 33 are dried with hot air and sterilized. The structure of the cap sterilization device 50 will be described below.

The product bottle carry-out unit 22 successively conveys the product bottles 35 including the caps 33 attached by the cap attaching device 16 to the outside of the content filling system 10.

The content filling system 10 includes the sterile chamber 13. The sterile chamber 13 houses the bottle sterilization device 11, the air-rinsing device 14, the sterile-water-rinsing device 15, the filling device 20, and the cap attaching device 16 described above. The content filling system 10 may be composed of, for example, a sterile filling system. In such a case, the interior of the sterile chamber 13 is maintained in a sterile state.

Alternatively, the content filling system 10 may be a high-temperature filling system that fills with the content at a high temperature of 85° C. or more and less than 100° C. Alternatively, the content filling system 10 may be a medium-temperature filling system that fills with the content at a medium temperature of 55° C. or more and less than 85° C.

(Cap Sterilization Device)

The structure of the above-described cap sterilization device 50 will now be described with reference to FIG. 2. FIG. 2 is a schematic front view of the cap sterilization device 50 according to the present embodiment. The upward and downward directions in FIG. 2 respectively correspond to vertically upward and downward directions.

As illustrated in FIG. 2, the cap sterilization device 50 includes an introduction chamber 51, a sterilant spraying chamber 52, an air-rinsing chamber 53, and a cleaning chamber 54. The introduction chamber 51, the sterilant spraying chamber 52, the air-rinsing chamber 53, and the cleaning chamber 54 are arranged in that order in a conveying direction of the caps 33. The chambers 51, 52, 53, and 54 are disposed in a housing 60.

The introduction chamber 51 and the sterilant spraying chamber 52 are separated from each other by a partition wall 61 provided therebetween. Similarly, the introduction chamber 51 and the air-rinsing chamber 53 are separated from each other by a partition wall 62. The sterilant spraying chamber 52 and the air-rinsing chamber 53 are separated from each other by a partition wall 63. The air-rinsing chamber 53 and the cleaning chamber 54 are separated from each other by a partition wall 64.

These partition walls 61, 62, 63, and 64 prevent gas or the like from flowing between the chambers 51, 52, 53, and 54, and serve to stabilize the pressures in the chambers 51, 52, 53, and 54. The partition walls 61, 62, 63, and 64 each have an opening large enough to allow the caps 33, for example, to pass therethrough. The openings have a minimum size, for example, about the size of one cap 33, to prevent variations in the pressures in the chambers 51, 52, 53, and 54.

A hopper 56, a sorter 57, and a cap inspection device 58 are disposed upstream of the introduction chamber 51 and outside the housing 60. A large number of caps 33 are randomly charged into the hopper 56 from the outside. The sorter 57 aligns the caps 33 that have been randomly charged into the hopper 56 in one or more lines, and conveys the caps 33 from a lower location toward an upper location in the vertical direction. The cap inspection device 58 inspects the shapes, for example, of the caps 33 and discharges the caps 33 that have failed the inspection. The caps 33 that have passed the inspection are conveyed in a line toward the introduction chamber 51.

Well-known caps that are substantially circular in plan view and have an opening in an inner surface are used as the caps 33. The caps 33 may be made of a thermoplastic resin, such as high-density polyethylene (HDPE), polypropylene (PP), or biodegradable plastic. The caps 33 may be general bottle caps, but may also be composite bottle caps or sport bottle caps.

The cap sterilization device 50 further includes a conveyance guide 70 along which the caps 33 that have passed the inspection are conveyed to the sterilant spraying chamber 52. The conveyance guide 70 causes the caps 33 to be conveyed in a line. The conveyance guide 70 may include, for example, a plurality of rails. In such a case, a space small enough to prevent the caps 33 from falling is formed in a region surrounded by the rails, and the caps 33 are conveyed through this space. This conveyance guide 70 is inclined with respect to a horizontal plane HS so that the caps 33 are conveyed from the introduction chamber 51 toward the sterilant spraying chamber 52 by their own weight. Since the conveyance guide 70 is provided, the caps 33 can be conveyed from the cap inspection device 58 to the sterilant spraying chamber 52 at a high speed. The conveyance guide 70 is provided with a first stopper 71, which is capable of being opened and closed, at a location inside the introduction chamber 51. When the first stopper 71 is opened, the caps 33 are conveyed to a sterilant spraying wheel 74 described below. When the first stopper 71 is closed, the caps 33 accumulate at this position. The first stopper 71 may instead be provided on the conveyance guide 70 at a location inside the sterilant spraying chamber 52.

The cap sterilization device 50 further includes a conveying chute 72 along which the caps 33 that have been subjected to air-rinsing are conveyed downstream. The conveying chute 72 may include, for example, a plurality of rails. In such a case, a space small enough to prevent the caps 33 from falling is formed in a region surrounded by the rails, and the caps 33 are conveyed through this space. The conveying chute 72 is provided with a second stopper 73 that is capable of being opened and closed. In the present embodiment, the second stopper 73 is provided on the conveying chute 72 at a location outside the cleaning chamber 54. When the second stopper 73 is opened, the caps 33 are conveyed to the cap attaching device 16 along the conveying chute 72. When the second stopper 73 is closed, the caps 33 accumulate at this position. The second stopper 73 is preferably positioned so that the conveying chute 72 is capable of accommodating all of the caps 33 in the introduction chamber 51, the sterilant spraying chamber 52, the air-rinsing chamber 53, and the cleaning chamber 54 when the second stopper 73 is closed.

The conveying chute 72 is inclined with respect to the horizontal plane HS. An inclination angle α by which the conveying chute 72 is inclined with respect to the horizontal plane HS is preferably 10° or more and 90° or less, and more preferably 20° or more and 90° or less. When the inclination angle α of the conveying chute 72 is 10° or more, the caps 33 can be easily conveyed by their own weight. More specifically, even when the ability of the caps 33 to be conveyed by their own weight is reduced due to reduction in weight, if the inclination angle α of the conveying chute 72 is 10° or more, the caps 33 can be conveyed by their own weight without using propulsion air or the like for conveying the caps 33 downstream. Therefore, energy can be saved. Since the caps 33 are conveyed along the conveying chute 72 after being sterilized, if propulsion air is used to convey the caps 33 downstream, the propulsion air needs to be sterile. In the present embodiment, the caps 33 can be conveyed by their own weight without using propulsion air or the like for conveying the caps 33 downstream. Therefore, the costs for sterilizing the caps 33 can be significantly reduced.

The structures of the chambers 51, 52, 53, and 54 will now be described in more detail.

The introduction chamber 51 introduces the caps 33 received from the cap inspection device 58 into the sterilant spraying chamber 52. The introduction chamber 51 is disposed on a side of the sterilant spraying chamber 52 and the air-rinsing chamber 53. A first hot air supplier 80a supplies sterile hot air to the introduction chamber 51. The sterile hot air supplied from the first hot air supplier 80a is blown against the caps 33 conveyed by the conveyance guide 70. In this case, the sterile hot air is blown against the caps 33 from the upstream side toward the downstream side in the conveying direction of the caps 33. When the sterile hot air is blown against the caps 33 from the upstream side toward the downstream side in the conveying direction of the caps 33, the conveyance of the caps 33 can be improved. Therefore, the caps 33 can be reliably conveyed downstream. The temperature of the sterile hot air is, for example, 40° C. or more and 170° C. or less. Accordingly, the temperature in the introduction chamber 51 is maintained at, for example, 30° C. or more and 80° C. or less. Therefore, condensation of the sterilant in the introduction chamber 51 is suppressed, and variations in the level of sterilization between the caps 33 due to the sterilant remaining on the caps 33 in the form of liquid can be prevented.

An exhaust pipe 51A is connected to the introduction chamber 51. Exhaust gas is discharged from the introduction chamber 51 through the exhaust pipe 51A. The exhaust pipe 51A is connected to a blower (not illustrated) that sucks gas from the exhaust pipe 51A. A scrubber (not illustrated) that processes a sterilant component in the gas is connected to the blower. The pressure in the introduction chamber 51 is maintained at a positive pressure (for example, 0 Pa or more and 200 Pa or less. As a result, the sterilant is prevented from flowing excessively into the introduction chamber 51.

In the sterilant spraying chamber 52, the sterilant is sprayed toward the caps 33 supplied by the conveyance guide 70. The sterilant is, for example, aqueous hydrogen peroxide. The sterilant spraying chamber 52 is disposed on a side of the introduction chamber 51. The pressure in the sterilant spraying chamber 52 is maintained at a positive pressure (for example, −20 Pa or more and 50 Pa or less). Accordingly, the sterilant is prevented from flowing excessively out of the sterilant spraying chamber 52.

The sterilant spraying chamber 52 has a bottom surface that is inclined with respect to a horizontal plane. More specifically, the bottom surface of the sterilant spraying chamber 52 is inclined downward toward the introduction chamber 51. A drain pipe 52A is connected to the bottom surface of the sterilant spraying chamber 52. Accordingly, liquid droplets generated in the sterilant spraying chamber 52 due to, for example, condensation and waste liquid can be discharged to the outside of the sterilant spraying chamber 52 through the drain pipe 52A. The drain pipe 52A is curved in an S-shape at an intermediate position thereof, and the waste liquid (sterilant (aqueous hydrogen peroxide, peracetic acid)) is accumulated in the S-shaped portion. Thus, a water seal mechanism is provided to separate a sterile area and a non-sterile area from each other. The liquid that constitutes the water seal mechanism may be sterile water. Alternatively, the water seal mechanism may be omitted, and the drain pipe 52A may be provided with a valve that separates the sterile area and the non-sterile area from each other.

The sterilant spraying wheel 74, which conveys the caps 33 while rotating the caps 33, is disposed in the sterilant spraying chamber 52. The sterilant spraying wheel 74 rotates (turns) around a rotation center axis that is parallel to a horizontal direction, and thereby rotates (revolves) the caps 33 to convey the caps 33. The sterilant spraying wheel 74 includes a star wheel (not illustrated) positioned at the center and a plurality of rails (not illustrated) disposed around the star wheel. The star wheel has cuts (not illustrated) for receiving the caps 33. Each of the rails serves to prevent the caps 33 from falling. The caps 33 are conveyed when the star wheel is driven, and are rotated (revolved) while being guided by the rails. By using the sterilant spraying wheel 74, the caps 33 can be conveyed at a high speed in the cap sterilization device 50.

The caps 33 fed along the conveyance guide 70 are received by the sterilant spraying wheel 74. Then, the caps 33 are conveyed by the sterilant spraying wheel 74 while the sterilant is sprayed thereonto by spraying nozzles 82A and 82B. Sterilant spraying devices 81A and 81B, which supply the sterilant to the caps 33, are disposed on a side of the sterilant spraying chamber 52. The sterilant spraying devices 81A and 81B are disposed in a housing space CS positioned below a protruding portion 53a, which will be described below. In the present embodiment, two sterilant spraying devices 81A and 81B are provided.

Figure 3:
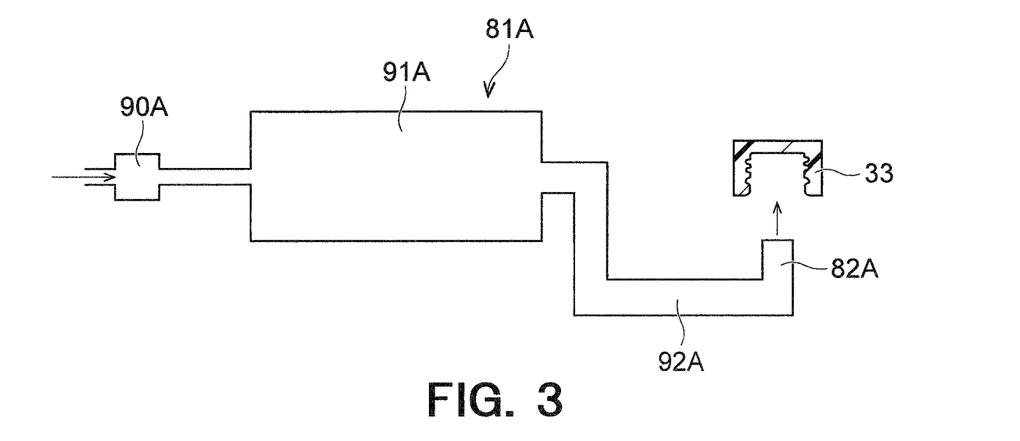
FIG. 3 is a schematic sectional view of a sterilant spraying device included in the cap sterilization device according to the embodiment of the present disclosure (sectional view taken along line in FIG. 2).

One sterilant spraying device 81A is connected to the inner-surface spraying nozzle 82A, which supplies the sterilant to the inner surfaces (openings) of the caps 33. As illustrated in FIG. 3, the sterilant spraying device 81A includes a supply spray 90A that supplies the sterilant and a heater 91A that heats the sterilant supplied from the supply spray 90A. A first supply pipe 92A that supplies the sterilant is connected to the heater 91A. The first supply pipe 92A is connected to the inner-surface spraying nozzle 82A that supplies the sterilant to the inner surfaces (openings) of the caps 33.

Figure 4:
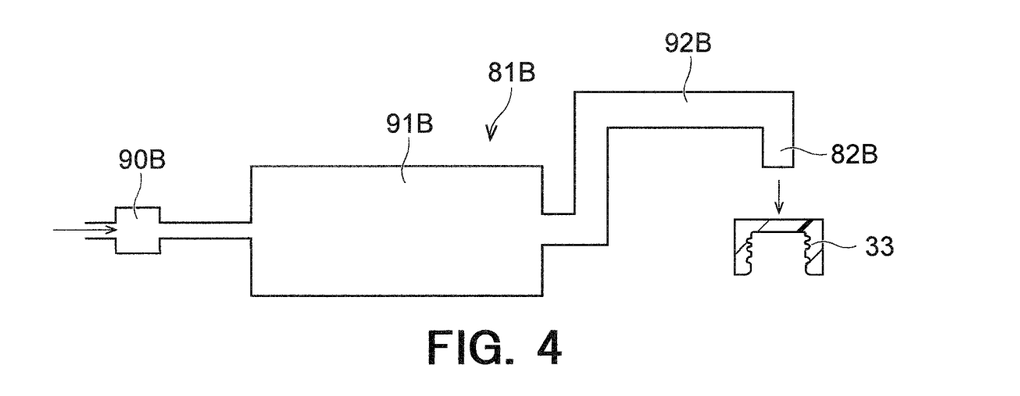
FIG. 4 is a schematic sectional view of a sterilant spraying device included in the cap sterilization device according to the embodiment of the present disclosure (sectional view taken along line IV-IV in FIG. 2).

The other sterilant spraying device 81B is connected to the outer-surface spraying nozzle 82B, which supplies the sterilant to the outer surfaces (top portions) of the caps 33. As illustrated in FIG. 4, the sterilant spraying device 81B includes a supply spray 90B that supplies the sterilant and a heater 91B that heats the sterilant supplied from the supply spray 90B. A second supply pipe 92B that supplies the sterilant is connected to the heater 91B. This second supply pipe 92B is connected to the outer-surface spraying nozzle 82B that supplies the sterilant to the outer surfaces (top portions) of the caps 33.

Thus, in the present embodiment, one sterilant spraying device 81A supplies the sterilant to the inner surfaces (openings) of the caps 33, and the other sterilant spraying device 81B supplies the sterilant to the outer surfaces (top portions) of the caps 33. In this case, the sterilant spraying device 81A and the sterilant spraying device 81B can be controlled individually. Therefore, the amount of sterilant sprayed onto the inner surfaces of the caps 33 and the amount of sterilant sprayed onto the outer surfaces of the caps 33, for example, can be adjusted as appropriate. Preferably, on the convey path of the sterilant spraying wheel 74, the sterilant is supplied to the inner surfaces of the caps 33 by the spraying nozzle 82A first, and then to the outer surfaces of the caps 33 by the spraying nozzle 82B.

Figure 5:
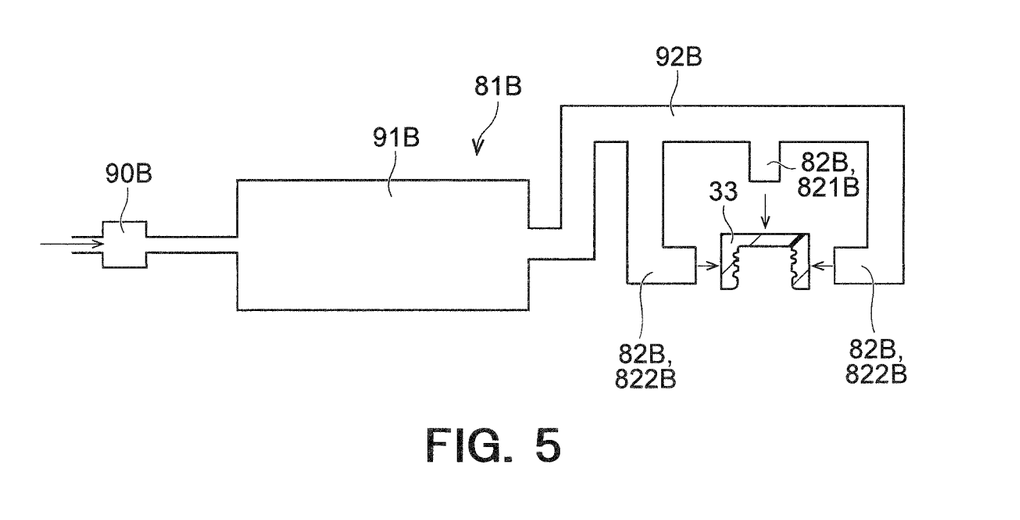
FIG. 5 is a schematic sectional view illustrating a modification of the sterilant spraying device included in the cap sterilization device according to the embodiment of the present disclosure.

As illustrated in FIG. 5, the sterilant spraying device 81B that supplies the sterilant to the outer surfaces (top portions) of the caps 33 may instead be structured such that the second supply pipe 92B is branched into three portions. In such a case, the spraying nozzle 82B may include a top spraying nozzle 821B and a pair of side spraying nozzles 822B. The top spraying nozzle 821B sprays the sterilant toward the top portions of the caps 33. The pair of side spraying nozzles 822B spray the sterilant toward the side surfaces of the caps 33. In this case, the side spraying nozzles 822B preferably spray the sterilant in a direction perpendicular to a direction of movement of the caps 33, but may instead spray the sterilant in a direction at an angle with respect to the direction of movement of the caps 33. When the spraying nozzle 82B includes the side spraying nozzles 822B, the side surfaces of the caps 33 can be sufficiently sterilized. The number of side spraying nozzles 822B may instead be one or three or more. Although not illustrated, a separate sterilant spraying device for spraying the sterilant toward the side surfaces of the caps 33 may also be provided.

Figure 6:
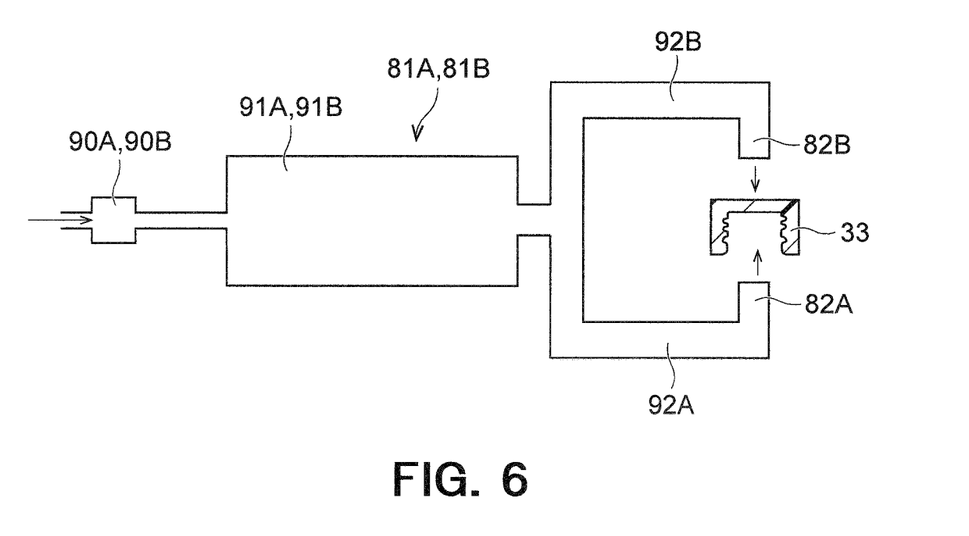
FIG. 6 is a schematic sectional view illustrating a modification of the sterilant spraying device included in the cap sterilization device according to the embodiment of the present disclosure.

As illustrated in FIG. 6, each of the sterilant spraying devices 81A and 81B may be configured to sterilize the inner and outer surfaces of the caps 33 simultaneously. In this case, as illustrated in FIG. 6, each of the heaters 91A and 91B is connected to a first supply pipe 92A and a second supply pipe 92B between which the sterilant is distributed. The first supply pipe 92A is connected to an inner-surface spraying nozzle 82A that supplies the sterilant to the inner surfaces (openings) of the caps 33. The second supply pipe 92B is connected to an outer-surface spraying nozzle 82B that supplies the sterilant to the outer surfaces (top portions) of the caps 33. When each of the sterilant spraying devices 81A and 81B sterilizes the inner and outer surfaces of the caps 33 simultaneously, the inner and outer surfaces of the caps 33 can be effectively sterilized.

A cover 83 that covers the spraying nozzles 82A and 82B is disposed around the spraying nozzles 82A and 82B. The cover 83 prevents scattering of the sterilant discharged from the spraying nozzles 82A and 82B, and allows the sterilant to be effectively sprayed onto the caps 33. A cleaning nozzle (not illustrated) is provided inside and/or outside the cover 83 to rinse off the sterilant, for example, that has adhered to the cover 83, the sterilant spraying wheel 74, and/or the partition wall 61 (hereinafter referred to also as the cover 83 and other components). The cover 83 and other components can be cleaned by using the cleaning nozzle.

The amount of hydrogen peroxide to be applied to sterilize the caps 33 is 0.6 µL/cm$^2$ or more and 4.7 µL/cm$^2$ or less (preferably 1.2 µL/cm$^2$ or more and 2.4 µL/cm$^2$ or less) when the concentration is 35% by weight. When the amount of hydrogen peroxide is in this range, the caps 33 can be sterilized at a high speed, and the chemical agent can be reliably removed in an air-rinsing process described below.

In the air-rinsing chamber 53, the caps 33 onto which the sterilant has been sprayed in the sterilant spraying chamber 52 is subjected to air-rinsing. The air-rinsing chamber 53 is disposed vertically above the sterilant spraying chamber 52. Since the air-rinsing chamber 53 is disposed vertically above the sterilant spraying chamber 52, the height of a fifth air-rinsing wheel 75e, which is one of air-rinsing wheels 75 described below that is connected to the above-described conveying chute 72, can be increased. Accordingly, the inclination angle α of the conveying chute 72 with respect to the horizontal plane HS can be increased. In addition, since the air-rinsing chamber 53 is disposed vertically above the sterilant spraying chamber 52, the sterilant (for example, hydrogen peroxide), whose relative density is greater than that of air, can be prevented from flowing into the air-rinsing chamber 53. The pressure in the air-rinsing chamber 53 is maintained at a positive pressure (for example, 30 Pa or more and 200 Pa or less, preferably 50 Pa or more and 150 Pa or less).

The air-rinsing chamber 53 includes a protruding portion 53a that protrudes sideways beyond the sterilant spraying chamber 52. The above-described sterilant spraying devices 81A and 81B are disposed in the housing space CS positioned below the protruding portion 53a. When the sterilant spraying devices 81A and 81B are disposed in the housing space CS positioned below the protruding portion 53a as described above, the size of the cap sterilization device 50 can be reduced. In the illustrated example, the sterilant spraying devices 81A and 81B are entirely disposed in the housing space CS. Accordingly, when maintenance of the cap sterilization device 50 is performed, the sterilant spraying devices 81A and 81B do not serve as obstructions. Thus, maintenance of the cap sterilization device 50 can be facilitated.

The bottom surface of the air-rinsing chamber 53 (bottom surface of the protruding portion 53a and the partition wall 63) is inclined with respect to a horizontal plane. More specifically, the bottom surface of the air-rinsing chamber 53 is inclined upward in the direction in which the protruding portion 53a protrudes (leftward in FIG. 2). A drain pipe 53A is connected to the bottom surface of the air-rinsing chamber 53. The drain pipe 53A is connected to the drain pipe 52A connected to the bottom surface of the sterilant spraying chamber 52. Accordingly, liquid droplets generated in the air-rinsing chamber 53 due to, for example, condensation can be discharged to the outside of the air-rinsing chamber 53 through the drain pipe 53A.

The air-rinsing wheels 75, which convey the caps 33 onto which the sterilant has been sprayed while rotating the caps 33, are disposed in the air-rinsing chamber 53. Plural air-rinsing wheels 75 are provided. In the present embodiment, a total of five air-rinsing wheels 75 are provided in the air-rinsing chamber 53. More specifically, a first air-rinsing wheel 75a, which receives the caps 33 from the sterilant spraying wheel 74, and second to fifth air-rinsing wheels 75b to 75e, which are disposed downstream of the first air-rinsing wheel 75a, are provided in the air-rinsing chamber 53. The first air-rinsing wheel 75a, the second air-rinsing wheel 75b, the third air-rinsing wheel 75c, the fourth air-rinsing wheel 75d, and the fifth air-rinsing wheel 75e are arranged in that order from the upstream side toward the downstream side in the conveying direction of the caps 33. The first air-rinsing wheel 75a is disposed to extend between the sterilant spraying chamber 52 and the air-rinsing chamber 53. The second to fifth air-rinsing wheels 75b to 75e are disposed in the air-rinsing chamber 53.

The air-rinsing wheels 75a to 75e rotate (turn) around respective rotation center axes La to Le that are parallel to a horizontal direction, and thereby rotate (revolve) the caps 33 to convey the caps 33. Each air-rinsing wheel 75 includes a star wheel (not illustrated) that is positioned at the center and that has cuts for receiving the caps 33, and a plurality of rails (not illustrated) that are disposed around the star wheel and that prevent the caps 33 from falling. The caps 33 are conveyed when the star wheel is driven, and are rotated (revolved) while being guided by the rails. By using the air-rinsing wheels 75, the caps 33 can be conveyed at a high speed in the cap sterilization device 50.

Each of the air-rinsing wheels 75b to 75e is disposed such that a corresponding one of the rotation center axes Lb to Le is positioned above the rotation center axes La to Ld of other air-rinsing wheels 75a to 75d that are positioned upstream of that air-rinsing wheel 75 in the conveying direction of the caps 33. More specifically, the rotation center axis Lb of the second air-rinsing wheel 75b is positioned above the rotation center axis La of the first air-rinsing wheel 75a positioned upstream of the second air-rinsing wheel 75b in the conveying direction of the caps 33. The rotation center axis Lc of the third air-rinsing wheel 75c is positioned above the rotation center axis Lb of the second air-rinsing wheel 75b. The rotation center axis Ld of the fourth air-rinsing wheel 75d is positioned above the rotation center axis Lc of the third air-rinsing wheel 75c. The rotation center axis Le of the fifth air-rinsing wheel 75e is positioned above the rotation center axis Ld of the fourth air-rinsing wheel 75d. Thus, each of the air-rinsing wheels 75b to 75e is disposed such that the corresponding one of the rotation center axes Lb to Le is positioned above the rotation center axes La to Ld of other air-rinsing wheels 75a to 75d that are positioned upstream of that air-rinsing wheel 75 in the conveying direction of the caps 33. Therefore, the height of the fifth air-rinsing wheel 75e can be increased, and the inclination angle α of the conveying chute 72 with respect to the horizontal plane HS can be increased. In addition, the rotation center axes La to Le of the air-rinsing wheels 75a to 75e are arranged in a staggered pattern in front view. Therefore, the width (dimension in the left-right direction in FIG. 2) of the air-rinsing chamber 53 can be reduced, and the size of the cap sterilization device 50 can also be reduced. In this case, the width of the air-rinsing chamber 53 may be about twice the diameter of the air-rinsing wheel 75.

Sterile hot air is blown against the inner and outer surfaces of the caps 33 while the caps 33 are successively conveyed by the air-rinsing wheels 75 in the air-rinsing chamber 53. The sterile hot air is introduced into the air-rinsing chamber 53 from second hot air suppliers 80b. In this case, the sterile hot air is blown against the caps 33 that pass through the air-rinsing wheels 75. In the present embodiment, each of the second to fifth air-rinsing wheels 75b to 75e is provided with one second hot air supplier 80b. Thus, the second hot air suppliers 80b are configured to blow the sterile hot air against the caps 33 conveyed by the second to fifth air-rinsing wheels 75b to 75e. The sterile hot air is not blown against the caps 33 conveyed by the first air-rinsing wheel 75a. The high-concentration sterilant (aqueous hydrogen peroxide) that has adhered to the caps 33 by condensation is retained on the caps 33 for a certain time on the first air-rinsing wheel 75a. Thus, the effect of sterilization by the sterilant can be increased. A retention time for which the sterilant that has adhered to the caps 33 by condensation is retained on the caps 33 is preferably 0.5 seconds or more and 5 seconds or less. When the retention time is 0.5 seconds or more, the effect of sterilization by the sterilant can be effectively increased. When the retention time is 5 seconds or less, an increase in the size of the first air-rinsing wheel 75a can be suppressed. Accordingly, an increase in the size of the air-rinsing chamber 53 and the cap sterilization device 50 can be suppressed. In addition, when the retention time is 5 seconds or less, a conveyance time for which the caps 33 are conveyed in the air-rinsing chamber 53 can be reduced. Therefore, a sterilization time for sterilizing the caps 33 in the cap sterilization device 50 can be reduced. The sterile hot air may also be blown against the caps 33 conveyed by the first air-rinsing wheel 75a. Also in such a case, the high-concentration sterilant (aqueous hydrogen peroxide) that has adhered to the caps 33 by condensation is retained on the caps 33 for a certain time in a section from the sterilant spraying devices 81A and/or 81B to the position at which air-rinsing is started. Thus, the effect of sterilization by the sterilant can be increased.

The temperature of the sterile hot air is, for example, 80° C. or more and 170° C. or less, preferably 90° C. or more and 120° C. or less. The flow rate of the sterile hot air is, for example, 5 m$^3$/min or more and 20 m$^3$/min or less. The time for which the sterile hot air is blown is 1 second or more and 20 seconds or less, preferably 3 seconds or more and 14 seconds or less. When the sterile hot air is blown against the caps 33, the temperature of the caps 33 is increased to 40° C. or more, preferably 50° C. or more. Thus, the sterilant that has adhered to the caps 33 is removed. The sterile hot air may contain a small amount of sterilant component, such as hydrogen peroxide.

A pipe 84 is provided to extend along the second to fifth air-rinsing wheels 75b to 75e. The sterile hot air is supplied to the pipe 84. The pipe 84 is disposed to face the caps 33 that are conveyed. In the present embodiment, the pipe 84 meanders in the direction of movement of the caps 33 in front view. The caps 33 move through the pipe 84 while the sterile hot air is blown thereagainst.

In the cleaning chamber 54, the caps 33 that have been subjected to air-rinsing in the air-rinsing chamber 53 are cleaned. The cleaning chamber 54 is disposed above the protruding portion 53a of the air-rinsing chamber 53. Accordingly, the size of the cap sterilization device 50 can be reduced. The caps 33 are conveyed along the conveying chute 72 in the cleaning chamber 54. While the caps 33 are being conveyed, first, a cleaning nozzle 85 sprays sterile water against the inner and outer surfaces of the caps 33. Accordingly, even when foreign matter has adhered to the caps 33, the foreign matter can be reliably removed. In addition, the caps 33 that have been heated by the sterile hot air can be cooled. Next, an air blow nozzle 86 blows sterile air against the inner and outer surfaces of the caps 33 to remove the sterile water. Even after the sterile air is blown against the caps 33, a small amount of sterile water remains on the caps 33. Accordingly, while the caps 33 are being conveyed along the conveying chute 72, appropriate lubrication is provided between the caps 33 and the conveying chute 72 to suppress an increase in the temperature of the caps 33 due to heat of friction between the conveying chute 72 and the caps 33. Since an increase in the temperature of the caps 33 is suppressed, the caps 33 can be reliably attached by the cap attaching device 16. The pressure in the cleaning chamber 54 is maintained at a positive pressure (for example, 5 Pa or more and 200 Pa or less). The pressure in the cleaning chamber 54 is lower than the pressure in a chamber (not illustrated) of the cap attaching device 16. Accordingly, the atmosphere including the sterilant is prevented from flowing out toward the cap attaching device 16.

The cleaning chamber 54 has a bottom surface that is inclined with respect to a horizontal plane. More specifically, the bottom surface of the cleaning chamber 54 is inclined downward in the direction in which the protruding portion 53a projects (leftward in FIG. 2). A drain pipe 54A is connected to the bottom surface of the cleaning chamber 54. Accordingly, liquid droplets generated in the cleaning chamber 54 can be discharged to the outside of the cleaning chamber 54 through the drain pipe 54A. The drain pipe 54A is curved in an S-shape at an intermediate position thereof, and waste liquid (sterile water) is accumulated in the S-shaped portion. Thus, a water seal mechanism is provided to separate a sterile area and a non-sterile area from each other. Alternatively, the water seal mechanism may be omitted, and the drain pipe 54A may be provided with a valve that separates the sterile area and the non-sterile area from each other. In the present embodiment, it is not necessary that the cleaning chamber 54 be provided. The caps 33 may be cleaned on the conveying chute 72 in a region outside the chambers 53 and 54 of the cap sterilization device 50. This is appropriate because droplets of the sterile water do not adhere to the air-rinsing wheels 75, and the interior the air-rinsing chamber 53 can be maintained in a dry state.

The cap attaching device 16 is disposed downstream of the conveying chute 72 of the cap sterilization device 50. To convey the caps 33 to the cap attaching device 16 along the conveying chute 72, the inclination angle α of the conveying chute 72 with respect to the horizontal plane HS is preferably greater than or equal to a predetermined value. To increase the inclination angle α of the conveying chute 72 with respect to the horizontal plane HS, the height of the air-rinsing wheel 75 to which the conveying chute 72 is connected (fifth air-rinsing wheel 75*e*) needs to be increased.

In the present embodiment, the air-rinsing chamber 53 is disposed vertically above the sterilant spraying chamber 52. Therefore, the height of the air-rinsing wheel 75 to which the conveying chute 72 is connected can be increased. Accordingly, the inclination angle α of the conveying chute 72 with respect to the horizontal plane HS can be increased. As a result, the size of the cap sterilization device 50 and the content filling system 10 can be reduced while reduction in the conveyance of the caps 33 along the conveying chute 72 is suppressed. In addition, since the inclination angle α of the conveying chute 72 with respect to the horizontal plane HS can be increased, the caps 33 can be conveyed by their own weight without using propulsion air (sterile air) for conveying the caps 33 downstream. Therefore, the costs for sterilizing the caps 33 can be significantly reduced.

Throughout the cap sterilization device 50, the conveyance rate of the caps 33 is 100 cpm or more and 1500 cpm or less, preferably 500 cpm or more and 1000 cpm or less. According to the cap sterilization device 50 of the present embodiment, the caps 33 can be reliably sterilized even when the caps 33 are conveyed at such a high rate. Here, cpm (caps per minute) is the number of caps 33 that passes a certain position in one minute. When a filling rate at which each bottle 30 is filled is low, such as when the bottles 30 are large (with an inner capacity of 1 L or more), the conveyance rate of the caps 33 can be reduced from the above-described rate in accordance with the filling rate. In such a case, conditions (temperature, flow rate, etc.) under which the hot air is supplied to the introduction chamber 51 and the air-rinsing chamber 53 may be adjusted to prevent an increase in the temperature of the caps 33.

(Content Filling Method)

A content filling method using the above-described content filling system 10 (FIG. 1) will now be described. In the following description, a filling method in an ordinary state, more specifically, a content filling method for filling the bottles 30 with a content, such as a beverage, to produce the product bottles 35 will be described.

First, the bottles 30 in an empty state are successively supplied to the bottle supplying unit 21 from the outside of the content filling system 10. The bottles 30 are conveyed from the bottle supplying unit 21 to the bottle sterilization device 11 by one of the conveying wheels 12.

Next, the bottle sterilization device 11 sterilizes the bottles 30 by using an aqueous hydrogen peroxide solution, which serves as a sterilant (sterilization step). The aqueous hydrogen peroxide solution is gas or mist obtained by temporarily vaporizing the aqueous hydrogen peroxide solution having a concentration of 1% by weight or more, preferably 35% by weight, and then condensing the vapor. The gas or mist is supplied to the bottles 30.

Subsequently, the bottles 30 are conveyed to the air-rinsing device 14 by another one of the conveying wheels 12. The air-rinsing device 14 supplies sterile heated air or room temperature air to activate the hydrogen peroxide and remove foreign matter, the hydrogen peroxide, etc. from the bottles 30 at the same time. Next, the bottles 30 are conveyed to the sterile-water-rinsing device 15 by another one of the conveying wheels 12. The sterile-water-rinsing device 15 performs cleaning using sterile water at 15° C. or more and 85° C. or less. More specifically, the sterile water at 15° C. or more and 85° C. or less is introduced into the bottles 30 at a flow rate of 5 L/min or more and 15 L/min or less. At this time, preferably, the bottles 30 are inverted, and the sterile water is introduced into the bottles 30 from the mouths that face downward. The sterile water flows out of the bottles 30 through the mouths. The sterile water is used to rinse off the hydrogen peroxide that has adhered to the bottles 30 and remove the foreign matter. The step of introducing the sterile water into the bottles 30 is not necessarily performed.

Subsequently, the bottles 30 are conveyed to the filling device 20 by another one of the conveying wheels 12. The filling device 20 fills the bottles 30 with the content through the mouths of the bottles 30 while rotating (revolving) the bottles 30 (filling step). The filling device 20 fills the sterilized bottles 30 with the content at a room temperature after the content, which is prepared in advance, is subjected to a heat sterilization process and cooled to the room temperature.

Subsequently, the bottles 30 filled with the content are conveyed to the cap attaching device 16 by another one of the conveying wheels 12.

The caps 33 are sterilized by the cap sterilization device 50 illustrated in FIG. 2 in advance (cap sterilization step). In this step, first, a large number of caps 33 are randomly charged into the hopper 56 from the outside of the cap sterilization device 50. Next, the caps 33 that have been randomly charged into the hopper 56 are aligned by the sorter 57, and then conveyed to the cap inspection device 58. Next, the cap inspection device 58 inspects the shape, for example, of each cap 33. The caps 33 that have passed the inspection are conveyed by the conveyance guide 70 in a line.

Next, the caps 33 are conveyed to the introduction chamber 51 and the sterilant spraying chamber 52 by the conveyance guide 70. Next, in the sterilant spraying chamber 52, the spraying nozzles 82A and 82B spray the sterilant, such as aqueous hydrogen peroxide, onto the caps 33 while the caps 33 are conveyed by the sterilant spraying wheel 74. Thus, the inner and outer surfaces of the caps 33 are sterilized.

Subsequently, the caps 33 onto which the sterilant has been sprayed are conveyed to the air-rinsing chamber 53. In the air-rinsing chamber 53, sterile hot air is blown against the inner and outer surfaces of the caps 33 while the caps 33 are successively conveyed by the five air-rinsing wheels 75. Thus, air-rinsing is performed to rinse off the sterilant that has adhered to the caps 33.

Next, the caps 33 are conveyed from the air-rinsing chamber 53 to the cleaning chamber 54. In the cleaning chamber 54, the cleaning nozzle 85 sprays sterile water against the caps 33 while the caps 33 are conveyed along the conveying chute 72, so that foreign matter, for example, that has adhered to the caps 33 is removed, and that the caps 33 are cooled. Subsequently, the air blow nozzle 86 blows sterile air against the caps 33 to remove the sterile water.

After that, the caps 33 are conveyed out of the cleaning chamber 54 and to the cap attaching device 16 along the conveying chute 72.

Referring to FIG. 1 again, the cap attaching device 16 attaches the caps 33 that haven been sterilized by the cap sterilization device 50 as described above to the mouths of the bottles 30 conveyed from the filling device 20. Thus, the product bottles 35 including the bottles 30 and the caps 33 are obtained (cap attaching step).

After that, the product bottles 35 are conveyed from the cap attaching device 16 to the product bottle carry-out unit 22, and are conveyed to the outside of the content filling system 10.

The above-described steps from the sterilization step to the cap attaching step are performed in a sterile atmosphere, that is, in a sterile environment, in the sterile chamber 13. After the sterilization process, sterile air at a positive pressure is supplied into the sterile chamber 13 so that sterile air continuously flows out of the sterile chamber 13.

The production (conveyance) rate of the bottles 30 in the content filling system 10 is preferably 100 bpm or more and 1500 bpm or less. Here, bpm (bottles per minute) corresponds to the conveyance rate of the bottles 30 in one minute.

As described above, according to the present embodiment, the sterilant spraying wheel 74 that conveys the caps 33 while rotating the caps 33 is disposed in the sterilant spraying chamber 52. In addition, the air-rinsing wheels 75 that convey the caps 33 onto which the sterilant has been sprayed while rotating the caps 33 are disposed in the air-rinsing chamber 53. In addition, the air-rinsing chamber 53 is disposed vertically above the sterilant spraying chamber 52. Therefore, the height of the air-rinsing wheel 75 to which the conveying chute 72 is connected can be increased. Accordingly, the inclination angle α of the conveying chute 72 with respect to the horizontal plane HS can be increased. As a result, the size of the cap sterilization device 50 and the content filling system 10 can be reduced while reduction in the conveyance of the caps 33 along the conveying chute 72 is suppressed. In addition, since the inclination angle α of the conveying chute 72 with respect to the horizontal plane HS can be increased, the caps 33 can be conveyed by their own weight without using propulsion air (sterile air) for conveying the caps 33 downstream. Therefore, the costs for sterilizing the caps 33 can be significantly reduced.

In addition, according to the present embodiment, plural air-rinsing wheels 75 are provided, and each of the air-rinsing wheels 75b to 75e is disposed such that the corresponding one of the rotation center axes Lb to Le is positioned above the rotation center axes La to Ld of other air-rinsing wheels 75a to 75d that are positioned upstream of that air-rinsing wheel 75 in the conveying direction of the caps 33. Accordingly, the height of the fifth air-rinsing wheel 75e can be more effectively increased, and the inclination angle α of the conveying chute 72 with respect to the horizontal plane HS can be further increased. As a result, reduction in the conveyance of the caps 33 along the conveying chute 72 can be more effectively suppressed.

In addition, according to the present embodiment, the air-rinsing chamber 53 includes the protruding portion 53a that protrudes sideways beyond the sterilant spraying chamber 52, and the sterilant spraying devices 81A and 81B that supply the sterilant to the caps 33 are provided on a side of the sterilant spraying chamber 52. The sterilant spraying devices 81A and 81B are disposed in the housing space CS positioned below the protruding portion 53a. Thus, the size of the cap sterilization device 50 can be reduced.

In addition, according to the present embodiment, the cleaning chamber 54 is disposed above the protruding portion 53a. Accordingly, the size of the cap sterilization device 50 can be further reduced.

(Modifications)

Figure 7:
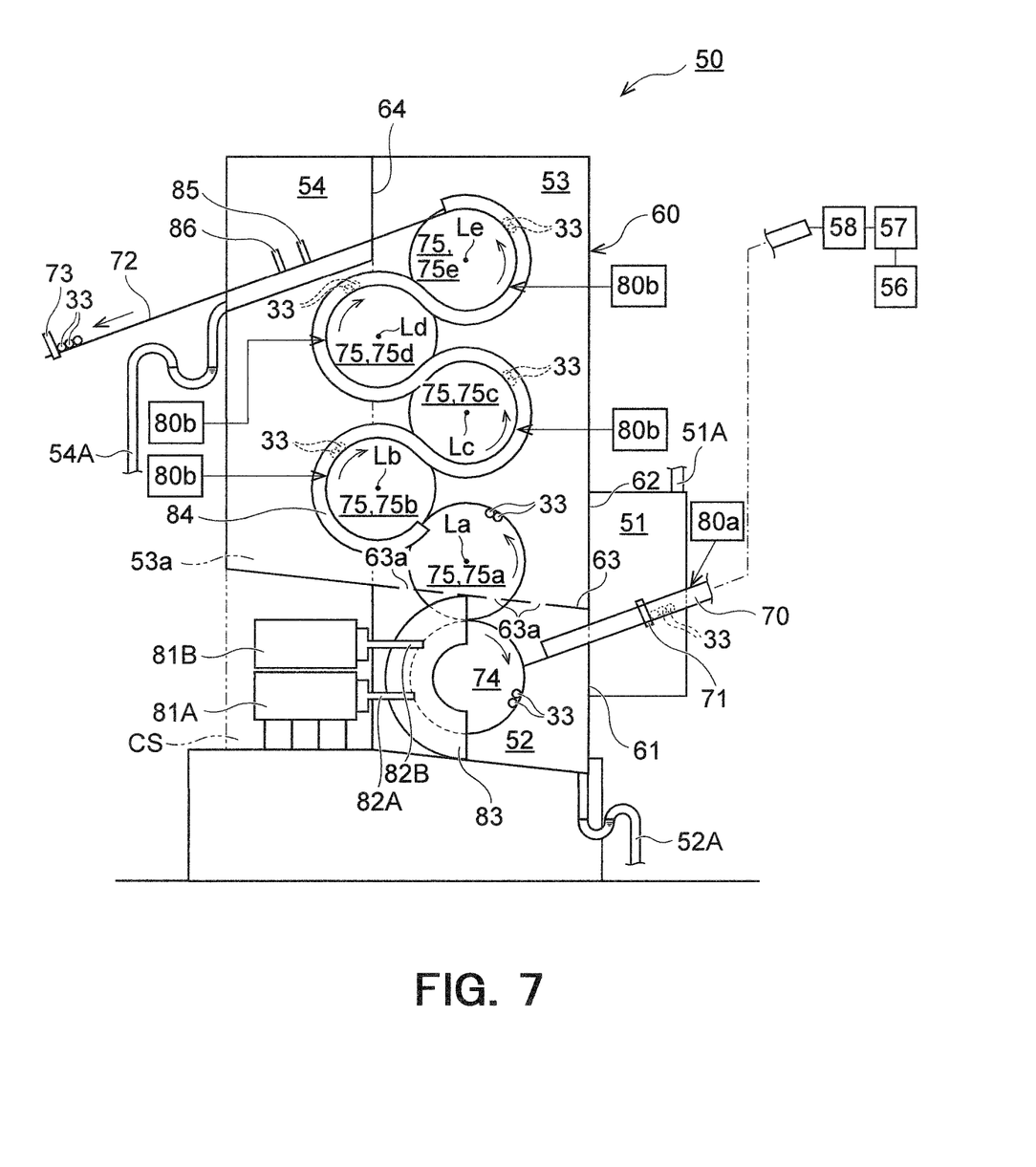
FIG. 7 is a schematic front view of a modification (first modification) of the cap sterilization device according to the embodiment of the present disclosure.
Figure 8:
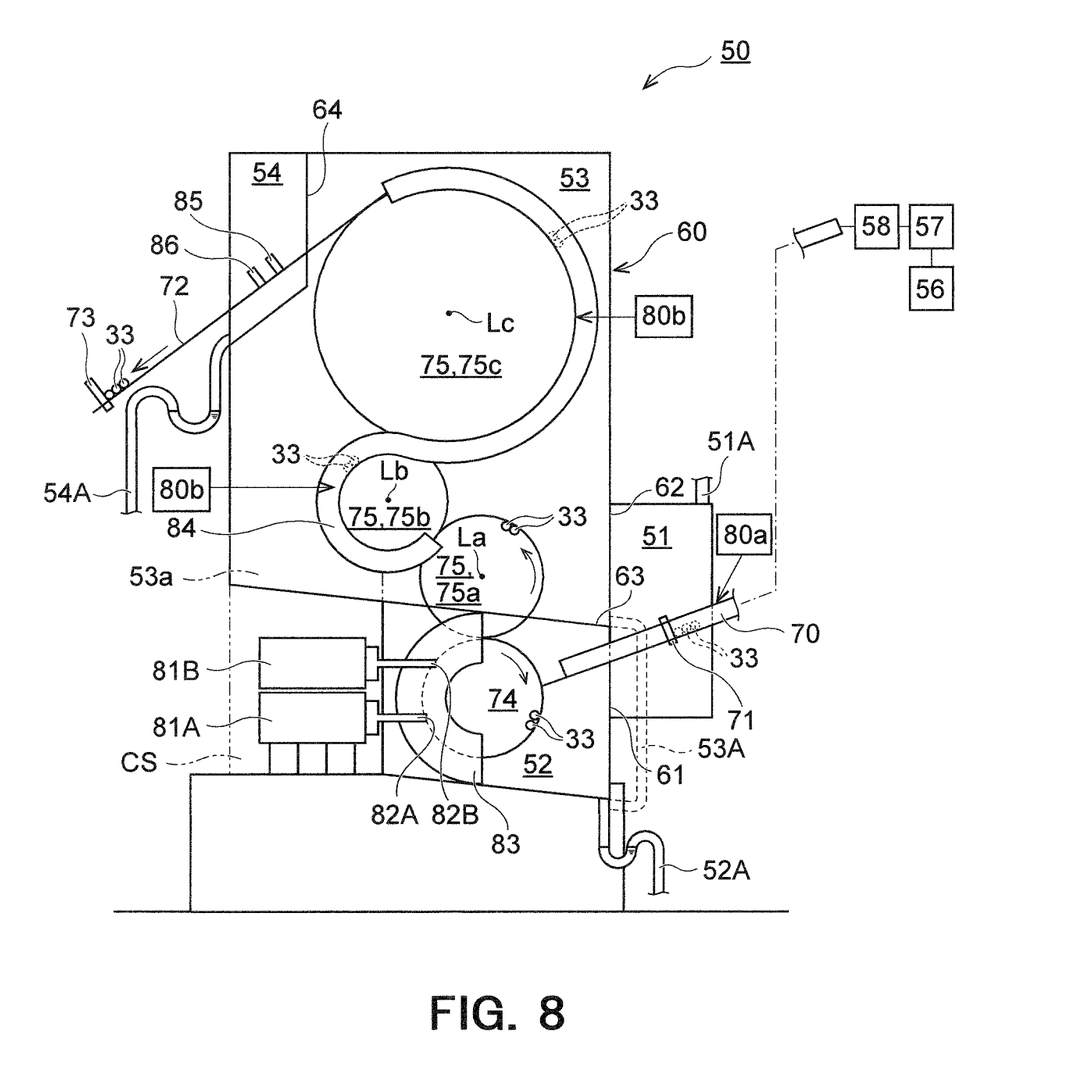
FIG. 8 is a schematic front view of a modification (second modification) of the cap sterilization device according to the embodiment of the present disclosure.
Figure 9:
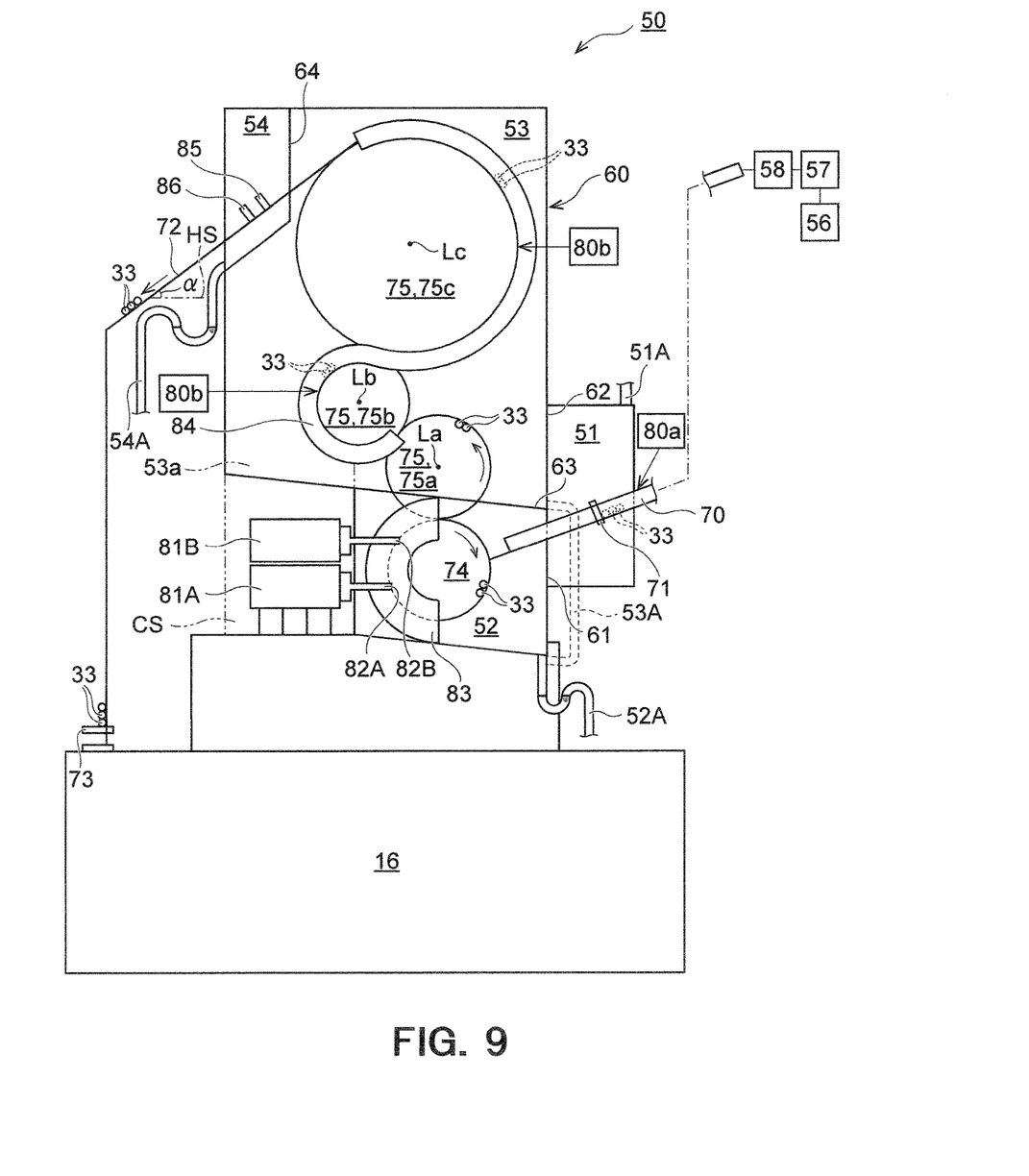
FIG. 9 is a schematic front view of a modification (third modification) of the cap sterilization device according to the embodiment of the present disclosure.

Modifications of the cap sterilization device according to the present embodiment will now be described with reference to FIGS. 7 to 9. In FIGS. 7 to 9, components that are the same as those in the embodiment illustrated in FIGS. 1 to 6 are denoted by the same reference signs, and detailed description thereof will be omitted.

FIG. 7 is a schematic front view (view corresponding to FIG. 2) of a cap sterilization device 50 according to a modification (first modification) of the present embodiment. Referring to FIG. 7, unlike the embodiment illustrated in FIGS. 1 to 6, the cap sterilization device 50 is configured to discharge liquid present in the air-rinsing chamber 53 through the sterilant spraying chamber 52. The liquid present in the air-rinsing chamber 53 may be sterilant (for example, peracetic acid) for sterilizing the caps 33 or cleaning water (sterile water) used for cleaning when the type of beverage to be filled is changed.

In this modification, the partition wall 63 has a plurality of openings 63a through which the air-rinsing chamber 53 and the sterilant spraying chamber 52 communicate with each other. The drain pipe 53A (see FIG. 2) is not connected to the bottom surface of the air-rinsing chamber 53. Accordingly, the liquid present in the air-rinsing chamber 53 is discharged from the drain pipe 52A through the sterilant spraying chamber 52. Any number of openings 63a may be formed in the partition wall 63. The openings 63a formed in the partition wall 63 may be arranged in a regular pattern or an irregular pattern.

At least one of the openings 63a is preferably disposed vertically above the cover 83 that surrounds the spraying nozzles 82A and 82B. Accordingly, when the liquid falls onto the bottom surface of the sterilant spraying chamber 52 as described below, the liquid can be brought into contact with the cover 83. Therefore, the liquid may be used to rise off the sterilant, for example, that has adhered to the cover 83 and devices positioned near the cover 83 (for example, the spraying nozzles 82A and 82B and the sterilant spraying wheel 74). In other words, the liquid may be used to clean the cover 83 and the devices positioned near the cover 83.

Stabilizing substances added to the sterilant (for example, hydrogen peroxide) may accumulate in the spraying nozzles 82A and 82B, the first supply pipe 92A (see FIG. 3) connected to the spraying nozzle 82A, and the second supply pipe 92B (see FIG. 4) connected to the spraying nozzle 82B (hereinafter referred to as the spraying nozzles 82A and 82B and other components). Therefore, when the type of the beverage to be filled is changed, the stabilizing substances that have accumulated in the spraying nozzles 82A and 82B and other components may be removed. In such a case, the spraying nozzles 82A and 82B and other components may be cleaned by using an acidic cleaning agent (nitric acid, phosphoric acid) or an alkaline cleaning agent (caustic soda, caustic soda containing chelating agent).

As described above, at least one of the openings 63a may be disposed vertically above the cover 83. In such a case, the liquid that falls onto the bottom surface of the sterilant spraying chamber 52 from the air-rinsing chamber 53 may be used to clean the cover 83 and the devices positioned near the cover 83. In other words, the liquid may be used to rinse off the acidic cleaning agent or the alkaline cleaning agent that has adhered to the cover 83, the spraying nozzles 82A and 82B, and other components. Therefore, the risk that the acidic cleaning agent or the alkaline cleaning agent will remain on the cover 83, the spraying nozzles 82A and 82B, and other components can be reduced.

In this modification, the liquid present in the air-rinsing chamber 53 flows along the inclined partition wall 63 and is supplied to the sterilant spraying chamber 52 through the openings 63a. At this time, the liquid present in the air-rinsing chamber 53 falls onto the bottom surface of the sterilant spraying chamber 52 through the openings 63a. After that, the liquid that has fallen onto the bottom surface of the sterilant spraying chamber 52 flows along the inclined bottom surface and reaches the drain pipe 52A. Then, the liquid that has reached the drain pipe 52A is discharged to the outside of the sterilant spraying chamber 52 through the drain pipe 52A. The liquid supplied to the sterilant spraying chamber 52 through the openings 63a may instead flow along the partition wall 63 and the partition wall 61, which separates the sterilant spraying chamber 52 and the introduction chamber 51 from each other, to the bottom surface of the sterilant spraying chamber 52. In addition, although not illustrated, the liquid supplied to the sterilant spraying chamber 52 may accumulate to a predetermined depth in the sterilant spraying chamber 52.

According to this modification, the cap sterilization device 50 is configured such that the liquid present in the air-rinsing chamber 53 is discharged through the sterilant spraying chamber 52. Accordingly, the liquid discharged through the sterilant spraying chamber 52 can be used to rinse off the sterilant and the like that have adhered to, for example, the cover 83, the sterilant spraying wheel 74, and/or the partition wall 61. Therefore, the number of cleaning nozzles (not illustrated) provided inside and/or outside the cover 83 to clean the cover 83 and other components can be reduced. When the number of cleaning nozzles in the sterilant spraying chamber 52 is reduced as described above, the risk that the beverage, for example, will enter the cleaning nozzles or spaces between the cleaning nozzles and other devices can be reduced. Therefore, for example, the sterilant spraying chamber 52 can be easily cleaned when the type of the beverage to be filled is changed. As a result, the cleanability of the sterilant spraying chamber 52 can be significantly increased. When the number of cleaning nozzles disposed in the cover 83 is reduced, the cap sterilization device 50 can be simplified, and the cost thereof can be reduced.

In the above-described modification, the partition wall 63 has the openings 63a through which the air-rinsing chamber 53 and the sterilant spraying chamber 52 communicate with each other, and the drain pipe 53A is not connected to the bottom surface of the air-rinsing chamber 53. However, the configuration is not limited to this. For example, although not illustrated, a drain pipe may be connected to the bottom surface of the air-rinsing chamber 53, and the liquid present in the air-rinsing chamber 53 may be supplied to the sterilant spraying chamber 52 through the drain pipe.

FIG. 8 is a schematic front view (view corresponding to FIG. 2) of a cap sterilization device 50 according to a modification (second modification) of the present embodiment. Referring to FIG. 8, unlike the embodiment illustrated in FIGS. 1 to 6, a total of three air-rinsing wheels 75 are provided in the air-rinsing chamber 53. More specifically, a first air-rinsing wheel 75a, which receives the caps 33 from the sterilant spraying wheel 74, and second and third air-rinsing wheels 75b and 75c, which are disposed downstream of the first air-rinsing wheel 75a, are provided in the air-rinsing chamber 53. In addition, the conveying chute 72 is connected to the third air-rinsing wheel 75c.

In this modification, the size of the third air-rinsing wheel 75c is greater than the size of the first air-rinsing wheel 75a and the second air-rinsing wheel 75b. The first air-rinsing wheel 75a and the second air-rinsing wheel 75b have the same size. However, the first air-rinsing wheel 75a and the second air-rinsing wheel 75b are not limited to this. For example, the size of the second air-rinsing wheel 75b may be greater than the size of the first air-rinsing wheel 75a.

According to this modification, the size of the third air-rinsing wheel 75c is greater than the size of the first air-rinsing wheel 75a and the second air-rinsing wheel 75b. Accordingly, the height of the third air-rinsing wheel 75c to which the above-described conveying chute 72 is connected can be easily increased. Therefore, the inclination angle α of the conveying chute 72 with respect to the horizontal plane HS can be more easily increased. In addition, since the number of air-rinsing wheels 75 can be reduced, the size of the cap sterilization device 50 can be reduced.

FIG. 9 is a schematic front view (view corresponding to FIG. 2) of a cap sterilization device 50 according to a modification (third modification) of the present embodiment. Referring to FIG. 9, unlike the second modification illustrated in FIG. 8, the cap sterilization device 50 is disposed vertically above the cap attaching device 16.

As described above, in the present embodiment, the rotation center axes La to Le of the air-rinsing wheels 75a to 75e are arranged in a staggered pattern in front view. Therefore, the width (dimension in the left-right direction in FIG. 2) of the air-rinsing chamber 53 can be reduced, and the size of the cap sterilization device 50 can also be reduced. Accordingly, as in this modification, the cap sterilization device 50 can be disposed vertically above the cap attaching device 16. When the cap sterilization device 50 is disposed vertically above the cap attaching device 16, the inclination angle α of the conveying chute 72 with respect to the horizontal plane HS can be further increased. In addition, for example, as illustrated in FIG. 9, a portion of the conveying chute 72 can be easily disposed to extend in a direction perpendicular to the horizontal plane HS. In this case, the caps 33 can be conveyed in a direction perpendicular to the horizontal plane HS. Therefore, the caps 33 can be reliably conveyed by their own weight without using propulsion air (sterile air) or the like for conveying the caps 33 downstream.

The components of the above-described embodiment and modifications may be applied in combination with each other as necessary. Also, some of the components of the above-described embodiment and modifications may be omitted.

The invention claimed is:

1. A cap sterilization device comprising:
    a sterilant spraying chamber in which a sterilant is sprayed onto a cap;
    an air-rinsing chamber in which the cap onto which the sterilant has been sprayed in the sterilant spraying chamber is subjected to air-rinsing, and
    a conveying chute along which the cap that has been subjected to air-rinsing is conveyed downstream,
    wherein a sterilant spraying wheel that conveys the cap while rotating the cap is disposed in the sterilant spraying chamber,
    wherein an air-rinsing wheel that conveys the cap onto which the sterilant has been sprayed while rotating the cap is disposed in the air-rinsing chamber, wherein the air-rinsing chamber is disposed vertically above the sterilant spraying chamber, wherein the conveying chute is provide with a stopper that is capable of being opened and closed, and wherein the stopper is positioned so that the conveying chute is capable of accommodating all of the caps in the sterilant spraying chamber and the air-rinsing chamber when the stopper is closed.

2. The cap sterilization device according to claim 1, wherein a plurality of the air-rinsing wheels are provided, and one of the air-rinsing wheels has a rotation center axis positioned above a rotation center axis of another one of the air-rinsing wheels that is positioned upstream of the one of the air-rinsing wheels in a conveying direction of the cap.

3. The cap sterilization device according to claim 1, wherein the air-rinsing chamber includes a protruding portion that protrudes sideways beyond the sterilant spraying chamber, and a sterilant spraying device that supplies the sterilant to the cap is disposed on a side of the sterilant spraying chamber, the sterilant spraying device being disposed in a housing space positioned below the protruding portion.

4. The cap sterilization device according to claim 3, further comprising a cleaning chamber in which the cap that has been subjected to air-rinsing in the air-rinsing chamber is cleaned, the cleaning chamber being disposed above the protruding portion.

5. The cap sterilization device according to claim 1, wherein liquid present in the air-rinsing chamber is discharged through the sterilant spraying chamber.

6. The cap sterilization device according to claim 1, wherein an inclination angle of the conveying chute with respect to a horizontal plane is 10° or more and 90° or less.

7. A content filling system comprising:
a bottle sterilization device that sterilizes a bottle;
a filling device that fills the bottle with a content;
the cap sterilization device according to claim 1 that sterilizes the cap; and
a cap attaching device that attaches the sterilized cap to a mouth of the bottle filled with the content by the filling device.

* * * * *